United States Patent [19]

Graziani et al.

[11] Patent Number: 4,550,217
[45] Date of Patent: Oct. 29, 1985

[54] CONVERSION OF METHANOL TO OLEFINS USING LARGE SIZE CATALYST PARTICLES

[75] Inventors: Kenneth R. Graziani, Thorofare; Ajit V. Sapre, West Deptford, both of N.J.

[73] Assignee: Mobil Oil Corporation, New York, N.Y.

[21] Appl. No.: 645,195

[22] Filed: Aug. 29, 1984

[51] Int. Cl.$^4$ .............................................. C07C 1/20
[52] U.S. Cl. .................... 585/324; 585/408; 585/469; 585/640; 585/733
[58] Field of Search ............... 585/408, 469, 640, 733, 585/324

[56] References Cited

U.S. PATENT DOCUMENTS

| | | | |
|---|---|---|---|
| 3,894,106 | 7/1975 | Chang et al. | 585/469 |
| 3,931,349 | 1/1976 | Kuo | 585/469 |
| 3,979,472 | 9/1976 | Butter | 585/640 |
| 3,998,898 | 12/1976 | Chang et al. | 585/469 |
| 4,025,571 | 5/1977 | Lago | 585/469 |
| 4,025,572 | 5/1977 | Lago | 585/469 |
| 4,025,575 | 5/1977 | Chang et al. | 585/640 |
| 4,052,472 | 10/1977 | Givens et al. | |
| 4,148,835 | 4/1979 | Chen et al. | 585/469 |
| 4,361,715 | 11/1982 | Short et al. | 585/640 |
| 4,441,990 | 4/1984 | Huang | 208/111 |

Primary Examiner—D. E. Gantz
Assistant Examiner—A. Pal
Attorney, Agent, or Firm—Alexander J. McKillop; Michael G. Gilman; Dennis P. Santini

[57] ABSTRACT

The present invention describes a methanol-to-chemical process for converting methanol to olefins using large catalyst particles. The large catalyst particles result in significant improvements in catalyst activity and reactor stability.

12 Claims, 1 Drawing Figure

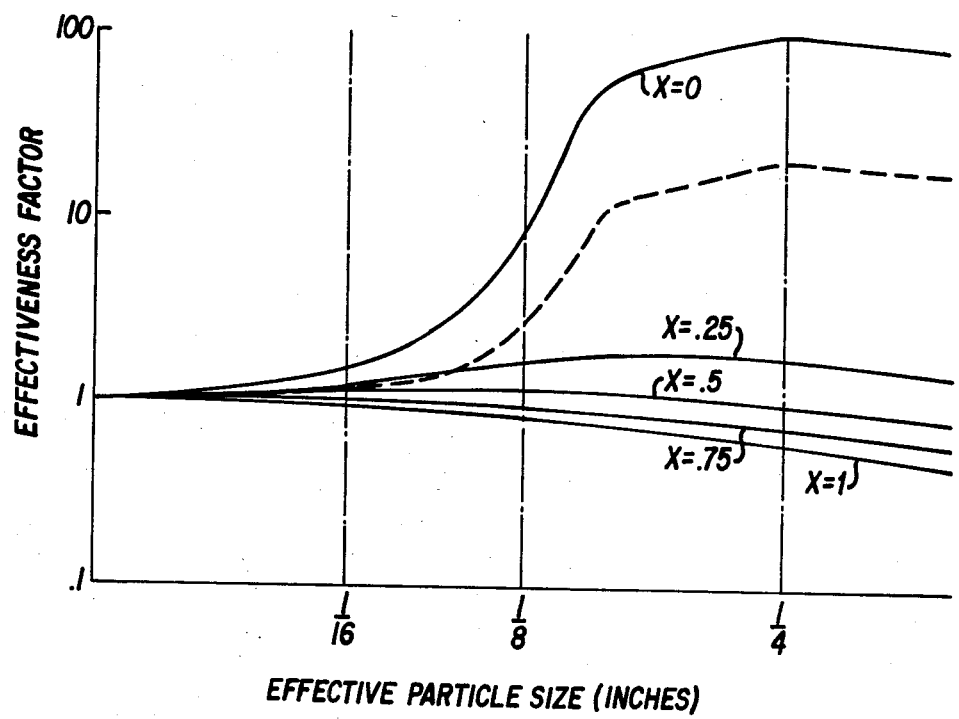

4,550,217

CONVERSION OF METHANOL TO OLEFINS USING LARGE SIZE CATALYST PARTICLES

BACKGROUND OF THE INVENTION

1. Field of the Invention

The present invention relates to the production of olefins from a feed comprising at least one lower aliphatic alcohol, e.g., methanol, its corresponding ether or mixtures thereof. More particularly, the invention relates to the catalytic conversion of the feed to an olefinic product using large size catalyst particles.

2. Description of Prior Art

The demand for olefinic feedstocks has increased rapidly in the past few years due to the increased need for synthetic fibers, plastics and petrochemicals. The increase in demand for olefinic feedstocks, such as ethylene and propylene, has periodically caused a shortage of these basic raw materials either because of a limitation in petroleum feedstocks of suitable quality or a limitation in the present olefinic production capacity. Thus, alternative sources of ethylene production from non-petroleum sources are required to keep pace with the demand for ethylene and other olefins.

It is now known that feed comprising lower alcohols and/or oxygenates thereof, such as methanol, ethanol, ether, (e.g., dimethyl ether), aldehydes and ketones, can be converted to gasoline grade hydrocarbons or to olefins by contacting the feed with zeolite catalysts.

U.S. Pat. No. 3,894,106 is directed to the production of olefins from aliphatic ethers by catalytic conversion with, for example, an HZSM-5 zeolite catalyst.

U.S. Pat. No. 3,979,472 is directed to the conversion of lower alcohols and their ethers with a composite of antimony oxide and a ZSM-5 zeolite to produce a mixture of ethylene, propylene and mononuclear aromatics.

U.S. Pat. No. 4,025,572 improved the processes for selecting ethylene by diluting a ZSM-5 zeolite with an inert diluent. A similar result is achieved through the use of subatmospheric partial pressure of the feed, according to U.S. Pat. No. 4,025,575.

U.S. Pat. No. 4,025,571 is directed to improved processes for selecting ethylene by employing a ZSM-5 zeolite in a large crystal form of at least about 1 micron.

U.S. Pat. No. 4,148,835 discloses the combination of the large crystal ZSM-5 zeolite and added metals.

The reaction is usually conducted in a fixed bed, in a fixed bed tubular reactor, or in a fluidized bed reactor. If the process, known as methanol-to-gasoline (MTG) or methanol-to-chemicals (MTC) process depending upon the product obtained, is conducted in a fixed bed or a fixed bed tubular reactor, it is usually carried out in two stages. The first stage comprises the conversion of the feed to dimethyl ether (DME) in the DME reactor, and the second stage the conversion of the effluent of the DME reactor to the gasoline-boiling point range hydrocarbons or to chemicals, such as olefins. Both stages of the reaction are carried out in the presence of a catalyst: the first stage with a gamma alumina catalyst (see, e.g., U.S. Pat. No. 3,931,349), and the second stage with an intermediate pore zeolite catalyst, such as, for example, ZSM-5. If the reaction is carried out in a fluidized bed reactor, the entire course of the reaction is catalyzed by an intermediate pore zeolite catalyst (see, e.g., U.S. Pat. No. 3,998,898). The intermediate pore zeolite catalysts used in the process are defined as zeolites which have a silica ($SiO_2$) to alumina ($Al_2O_3$) mole ratio of at least 12, a Constraint Index of about 1 to 12 and a crystal density of at least 1.6 grams per cubic centimeter ($g/cm^3$).

The conversion reaction of methanol to hydrocarbon products rich in ethylene and other light olefins (MTC process) is known to be autocatalytic on certain zeolite catalysts. This means that the light olefin products initially formed from methanol act as agents accelerating the methanol conversion reaction process. The selectivity of light olefins from methanol in an MTC process is inversely related to methanol partial pressure. Thus, in order to maximize light olefin production, lower MTC reactor operating pressures are desirable.

It is an object of this invention to maximize light olefin conversion from methanol, DME or mixtures of methanol and DME. This and other objects will be apparent in the following description of the subject invention.

SUMMARY OF THE INVENTION

In accordance with the present invention, it has been found that, in the catalytic conversion of alcohols to hydrocarbon contents, the proportion of olefinic hydrocarbons in the product stream can be desirably and dramatically increased by contacting the vaporous alcohol with a zeolite catalyst having an increased particle size. Of particular significance is the production of olefins at high rates of conversion from methanol feedstocks utilizing crystalline silicate zeolite catalysts, wherein the average size of the zeolite catalyst is dependent upon the conversion level of the feedstock. In one embodiment, the catalyst comprises a crystalline zeolite having an average particle size greater than about ⅛" in diameter.

The conversion is carried out by passing a feed comprising one or more compounds selected from the group consisting of lower monohydric alchols with up to 4 carbon atoms and their simple and fixed ether derivatives over a catalyst contained in a reaction zone. An effluent comprising a mixture of light olefins, paraffin hydrocarbons and aromatic hydrocarbons is withdrawn from the reaction zone. The light olefins are then segregated from the effluent.

DESCRIPTION OF THE DRAWING

The FIGURE illustrates the effectiveness of the catalyst particle size at various locations in the reactor.

DESCRIPTION OF THE PREFERRED EMBODIMENTS

The present invention relates to improvements in the catalytic conversion of methanol, its corresponding ether, i.e., DME, or mixtures thereof, to olefinic hydrocarbons. Methanol is preferred and may be substantially pure, industrial grade anhydrous methanol or even crude methanol containing usually 12 to 20 wt. % of water. Diluents may be included in the alcohol feed. Diluents include, but are not limited to: steam, hydrogen, helium, nitrogen, carbon dioxide, methane, ethane, propane, butane, pentane, hexane, heptane and flue gas.

The mixtures of crystalline zeolites utilized in the particular embodiment are members of a novel class of zeolite materials which exhibit unusual properties. Although these zeolites have unusually low alumina contents, i.e., high silica-to-alumina mole ratios, they are very active for many reactions, e.g., cracking, even when the silica-to-alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g., of the X and A type. Furthermore, carbonaceous deposits, when formed, may be removed by burning at higher than usual temperatures to restore activity. These zeolites, used as catalysts, generally have low cokeforming activity and therefore are conducive to long times on stream between regenerations by burning carbonaceous deposits with oxygen-containing gas, such as air.

For purposes of this invention, the term "zeolite" is meant to represent the class of porotectosilicates, i.e., porous crystalline silicates that contain silicon and oxygen atoms as the major components. Other components may be present in minor amounts, usually less than 14 mole % and preferably less than 4 mole %. These components include aluminum, gallium, iron, boron and the like, with aluminum being preferred, and used herein for illustration purposes. The minor components may be present separately or in mixtures.

The silica-to-alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica-to-alumina mole ratio of at least 12 are useful, it is preferred in some instances to use zeolites having much higher silica-to-alumina mole ratios, i.e., ratios of up to at least 500:1 and higher. In fact, zeolites as otherwise characterized herein but which are substantially free of aluminum, i.e., having silica-to-alumina mole ratios up to and including infinity, are found to be useful and even preferable in some instances. Such "high silica" zeolites are intended to be included within this description. The novel class of zeolites, after activation, acquire an intracrystalline sorption affinity for normal hexane which is greater than that for water, i.e., they exhibit "hydrophobic" properties.

The silica-alumina ratios referred to in this specification are the structural or framework ratios, that is, the ratio for the $SiO_4$ to the $AlO_4$ tetrahedra, which together constitute the structure of which the zeolite is composed. This ratio may vary from the silica-alumina ratio determined by various physical and chemical methods. For example, a gross chemical analysis may include aluminum, which is present in the form of cations associated with the acidic sites on the zeolite, thereby giving a low silica-alumina ratio. Similarly, if the ratio is determined by thermogravimetric analysis (TGA) of ammonia desorption, a low ammonia titration may be obtained if cationic aluminum prevents exchange of the ammonium ions onto the acidic sites. These disparities are particularly troublesome when certain treatments, such as the dealuminization methods described below which result in the presence of ionic aluminum free of the zeolite structure, are employed. Due care should therefore be taken to ensure that the framework silica-alumina ratio is correctly determined.

The class of zeolites useful herein are termed medium or intermediate pore zeolites and have an effective pore size of generally less than about 6 angstroms, such as to freely sorb normal hexane. Representative zeolites are the ZSM-5 family of zeolites. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of a particular zeolite solely from theoretical structural considerations.

A convenient measure of the extent to which a zeolite provides control molecules of varying sizes to its internal structure is the Constraint Index of the zeolite. Zeolites which provide a highly restricted access to and egress from its internal structure have a high value for the Constraint Index, and zeolites of this kind usually have pores of small size. On the other hand, zeolites which provide relatively free access to the internal zeolite structure have a low value for the Constraint Index. The method by which Constraint Index is determined is described fully in U.S. Pat. No. 4,016,218, to which reference is made for details of the method.

Constraint Index (CI) values for some typical materials are:

|  | CI |
| --- | --- |
| ZSM-4 | 0.5 |
| ZSM-5 | 6–8 |
| ZSM-11 | 6–8 |
| ZSM-12 | 2 |
| ZSM-20 | 0.5 |
| ZSM-23 | 9.1 |
| ZSM-34 | 30–50 |
| ZSM-35 | 4.5 |
| ZSM-38 | 2 |
| ZSM-48 | 3.5 |
| TMA Offretite | 3.7 |
| TEA Mordenite | 0.4 |
| Clinoptilolite | 3.4 |
| Beta | 0.6–1.2 |
| Mordenite | 0.5 |
| REY | 0.4 |
| Amorphous Silica-Alumina | 0.6 |
| Dealiminized Y (Deal Y) | 0.5 |
| Chlorinated Alumina | *1 |
| Erionite | 38 |

*Less Than

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables, such as crystal size of the zeolite, the presence of occluded contaminants, etc., may effect the Constraint Index. Therefore, it will be appreciated that it may be possible to so select test conditions as to establish more than one value for the Constraint Index of a particular zeolite. This explains the range of Constraint Index for zeolites, such as ZSM-5, ZSM-12, ZSM-34 and Zeolite Beta.

It should be understood that the Constraint Index value as used herein is an inclusive rather than an exclusive value. That is, a crystalline zeolite, when identified by any combination of conditions within the testing definition set forth herein as having a Constraint Index in the range of 1 to 12, is intended to be included in the instant novel zeolite definition, whether or not the same identical zeolite, when tested under other of the defined conditions, may give a Constraint Index value outside of the range of 1 to 12.

Examples of suitable zeolites with their corresponding Constraint Index include but are not limited to:

| First Component | Constraint Index |
| --- | --- |
| ZSM-5 | 6–8 |
| ZSM-11 | 6–8 |
| ZSM-12 | 2 |
| ZSM-22 | 7.3 |
| ZSM-23 | 9 |
| ZSM-35 | 4.5 |
| ZSM-38 | 2 |
| ZSM-48 | 3.5 |
| TMA Offretite | 3.7 |
| Clinoptilolite | 3.4 |

ZSM-5 is described in greater detail in U.S. Pat. No. 3,702,886 and U.S. Pat. No. Re. 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 is described in U.S. Pat. No. 4,397,827, the disclosure of which is incorporated herein by reference.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica-to-alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts, followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type of catalyst by base exchange with ammonium salts, followed by calcination in air, at about 540° C. for from about 15 minutes to about 24 hours.

Natural zeolites may sometimes be converted to zeolite structures of the class herein identified by various activation procedures and other treatments, such as base exchange, steaming, alumina extraction and calcination, alone or in combination. Natural minerals may be so treated include ferrierite, brewsterite, stilbite, dachiardite, epistilbite, hepulandite, and clinoptilolite.

If preferred, the zeolite of the present invention may include a hydrogenation-dehydrogenation component (referred to, for convenience, as a hydrogenation component) which is generally a metal or metals of groups IB, IIB, VA, VIA or VIIIA of the Periodic Table (IUPAC and U.S. National Bureau of Standards approved Table, as shown, for example, in the Chart of the Fisher Scientific Company, Catalog No. 5-702-10). The preferred hydrogenation components are the noble metals of Group VIIIA, especially platinum; but other noble metals, such as palladium, gold, silver, rhenium or rhodium, may also be used. Combinations of noble metals, such as platinum-rhenium, platinum-palladium, platinum-iridium or platinum-iridium-rhenium, together with combinations of non-noble metals, particularly of Groups VIA and VIIIA, are of interest, particularly with metals such as cobalt, nickel, vanadium, tungsten, titanium and molybdenum, for example, platinum-tungsten, platinum-nickel or platinum-nickel-tungsten. Base metal hydrogenation components may also be used, especially nickel, cobalt, molybdenum, tungsten, copper or zinc. Combinations of base metals, such as cobalt-nickel, cobalt-molybdenum, nickel-tungsten, cobalt-nickel-tungsten or cobalt-nickel-titanium, may also be used.

The metal may be incorporated into the catalyst by any suitable method, such as impregnation or exchange, onto the zeolite. The metal may be incorporated in the form of a cationic, anionic or a neutral complex, such as $Pt(NH_3)_4^{2+}$, and cationic complexes of this type will be found convenient for exchanging metals onto the zeolite. Anionic complexes are also useful for impregnating metals into the zeolites.

The amount of the hydrogenation-dehydrogenation component is suitably from 0.01 to 25% by weight, normally 0.1 to 5% by weight, especially for noble metals, and preferably 0.3 to 1% by weight, although this will, of course, vary with the nature of the component. For example, less of the highly active noble metals, particularly platinum, is required than of the less active metals.

The original cations associated with each of the crystalline silicate zeolites utilized herein may be replaced by a wide variety of other cations according to techniques well known in the art. Typical replacing cations include hydrogen, ammonium, alkyl ammonium and metal cations, including mixtures of the same. Of the replacing metallic cations, particular reference is given to cations of metals, such as the rear earth metals or manganese, as well as metals of Groups IIA and B of the Periodic Table, e.g., zinc, and Group VIII of the Periodic Table, e.g., nickel, platinum and palladium.

Typical ion exchange techniques are to contact the particlar zeolite with a salt of the desired replacing cation. Although a wide variety of salts can be employed, particular preference is given to chlorides, nitrates and sulfates. Representative ion exchange techniques are disclosed in a wide variety of patents, including U.S. Pat. Nos. 3,140,249; 3,140,251; and 3,140,253.

Alternatively, the metallic catalyst component can be incorporated into the zeolite by impregnating the zeolite with a solution of the metal or metal compounds or complexes, followed by stripping of the solvent employed. Metallic compound incorporation can also be accomplished by sorbing metal compounds or complexes into the zeolite. Thus, such materials as nickel carbonyl or rhodium carbonyl chloride can be sorbed from solution or from the gas phase into the zeolite structure.

Following contact with a solution of the desired replacing cation, the zeolite is then preferably washed with water and dried at a temperature ranging from 150° F. (70° C.) to about 600° F. (320° C.) and thereafter calcined in air, or other inert gas, at temperatures ranging from about 500° F. (230° C.) to 1500° F. (820° C.) for periods of time ranging from 1 to 48 hours or more. It has been further found that catalysts of improved selectivity and other beneficial properties may be obtained by subjecting the zeolite to treatment with steam at elevated temperatures ranging from 500° F. (230° C.) to 1200° F. (650° C.), and preferably 750° F. (400° C.) to 1000° F. (540° C.). The treatment may be accomplished in an atmosphere of 100% steam or an atmosphere consisting of steam and a gas which is substantially inert to the zeolites. A similar treatment can be accomplished at lower temperatures and elevated pressure, e.g., 350°–700° F. (180°–370° C.) at 10 to about 200 atmospheres.

The crystalline silicate zeolite utilized in the process of this invention is desirably employed in intimate combination in an amount between 0.1 and about 25% by weight with one or more hydrogenation components, such as tungsten, vanadium, zinc, molybdenum, rhenium, nickel, cobalt, chromium, manganese, or a noble metal such as platinum or palladium. Such component can be exchanged into the composition, impregnated thereon or physically intimately admixed therewith. In the case of platinums, impregnation occurs by treating the zeolite with a platinum metal-containing ion. Suitable platinum compounds include chloroplatinic acid, platinous chloride and various compounds containing the platinum amine complex.

The compounds of the useful platnium or other metals can be divided into compounds in which the metal is present in the cation of the compound and compounds in which it is present in the anion of the compound. Both types of compounds which contain the metal in the ionic state can be used. A solution in which platinum metals are in the form of a cation or cationic complex, e.g., $Pt(NH_3)_4Cl_2$, is particularly useful.

Prior to use, the zeolites should be dehydrated at least partially. This can be done by heating to a temperature in the range of 390°–1110° F. (200°–600° C.) in an inert atmosphere, such as air, nitrogen, etc., and at atmospheric or substmospheric pressures for between 1 and 48 hours. Dehydration can also be performed at lower temperatures merely by using a vacuum, but a longer time is required to obtain sufficient amount of dehydration.

The preferred zeolites useful with respect to this invention are those having a Constraint Index, as defined above, of about 1 to about 12, a silica-to-alumina mole ratio of at least about 12 and a dried crystal density of not less than about 1.6 grams per cubic centimeter. The dry density for known structures may be calculated from the number of silicon plus aluminum atoms per 1000 cubic angstroms, as given, e.g., on page 19 of the article "Zeolite Structure" by W. M. Meier. This paper, the entire contents of which are incorporated herein by reference, is included in *Proceedings of the Conference on Molecular Sieves* (London, April 1967), published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5% by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials, such as clay, silica and/or metal oxides. The latter may be either naturally occurring or in the form of gelatinous precipitates or gels, including mixtures of silica and metal oxides. Naturally occurring clays which can be composited with the zeolite include those of the montmorillonite and kaolin families, which families include the sub-bentonites and the kaolin families, which families include the sub-bentonites and the kaolins commonly known as Dixie, McNamee-Georgia and Florida clays, or others in which the main mineral constituent is halloysite, kaolinite, dickite, nacrite or anauxite. Such clays can be used in the raw state, as originally mined or initially subjected to calcination, acid treatment or chemical modification.

The present invention centers on the discovery that catalyst activity in a reactor is increased with increased catalyst particle size, wherein the average particle size of the catalyst depends upon the conversion level of the feedstock. Catalyst particles sizes in the range of $\frac{1}{8}''$ (0.3 cm) are contemplated. Prior to this unexpected discovery, it was believed that catalyst activity increased with decreasing particle size.

While not wishing to be limited by any theory, it is believed that the increase in activity for larger zeolite containing catalyst particles is the result of the interaction between the diffusion of gases into the catalyst particles and the autocatalysis effect generated by the presence of olefins in the porous particles. The light olefin products initially formed from methanol act as autocatalytic agents, accelerating the methanol conversion reaction. In this type of reaction, if the catalyst particle is large enough, there would be concentration gradients within the catalyst particle due to diffusion. If a catalyst particle is large enough to have significant concentration gradients of diffusing species, i.e., the methanol reactant and hydrocarbon products, an interaction of methanol and light olefin products would be formed within the particle, resulting in higher observed activity for methanol conversion. Thus, the interaction of autocatalysis and diffusion would lead to increased activity which can be used effectively to improve the MTC process.

In addition to the improvement in activity, the large size catalyst particles present the advantage of lower pressure drops through a fixed bed of catalyst. It is generally known that with a methanol charge, elevated pressures tend to produce increased quantities of 1,2,4,5-tetramethylbenzene (durene), an undesirable by-product, while lower pressures, e.g., less than 50 psig, favor the production of light olefins. Thus, in order to maximize light olefin production, lower MTC reactor operating pressures are desirable. A minimum average reactor pressure is directly relates to fixed-bed pressure drop. Therefore, a practical means of achieving lower pressure drop and lower reactor pressure is to increase catalyst particle size. The use of larger catalyst particles will give a higher activity and allow for the operation of the process at lower pressures.

The conversion process described herein may be carried out as a batch-type, semi-continuous or continuous operation utilizing a fixed or moving bed reactor conducted to a regeneration zone, wherein coke is burned from the catalyst in an oxygen-containing atmosphere, e.g., air, at an elevated temperature, after which the regenerated catalyst is recycled to the conversion zone for further contact with the chargestock. In a fixed bed reactor, regeneration is carried out in a conventional manner, where an inert gas containing a small amount of oxygen (0.5-2%) is used to burn the coke in a controlled manner so as to limit the temperature to a maximum of around 300°-500° C.

For purposes of the present invention, the preferred alcohol feed is methanol and subsequent discussion of the conversion process will be with reference to the methanol feedstock. However, it is to be understood that such reference is intended to be for purposes of illustrating the invention and should not be taken as limiting the novel process disclosed herein.

The methanol feed is passed over the catalyst at a rate of 0.5-10 WHSV (weight hourly space velocity), preferably at 1-5 WHSV. In all cases, the WHSV is calculated on the pounds of methanol feed per hour per pound of catalyst. Because it is well known that high operating pressures result in reduced yields of light olefins, the inlet pressure to the reactor should be less than 100 psig, preferably less than 40 psig, and most preferably about 25 psig. The conversion is carried out at temperatures between about 480° F. (250° C.) and 790° F. (420° C.), with the preferred operating temperature range being between 530° F. (275° C.) and 700° F. (375° C.). It is understood that the temperatures referred to herein are the maximum temperature within the reaction zone. Thus, in a fixed bed operation, the inlet temperature may be lower than 480° F. (250° C.).

Within the prescribed conditions, a conversion per pass of from 5% to about 90% of the methanol may be achieved and the ratio of $C_2$-$C_4$ olefins to paraffins in the product mix is significantly enhanced. The term "conversion", as used herein, is to be understood to mean a chemical change in which a hydrocarbon having at least 2 carbon atoms is formed. Thus, a substantially pure methanol feed will initially form an equilibrium mixture of alcohol, DME and water, which is then further converted to a mixture of hydrocarbons and water. This DME is ignored in computing conversion, since no new carbon-carbon bonds are created in its formation. If some DME is present in the methanol feed, its conversion to hydrocarbons is added to that of the methanol to arrive at the "conversion" value. Specifically, 80% conversion as used herein means that 80% of the total-$CH_2$-groups present in the methanol and DME of the methanol feed are converted to hydrocarbons.

It has now been discovered that the size of the catalyst particle is dependent upon the conversion level of the feedstock. Thus, a 50% conversion level may command the use of a catalyst particle of a size which is different from a 10% conversion level. Further discussions and examples relating to this follow.

After the catalyst has been on stream for a sufficient time to accumulate inactivating deposits and is no longer effective, its activity may be restored by contact with oxygen-containing gas at sufficiently elevated temperature to burn away the deposits.

The hydrocarbon mixture produced by the process of this invention is recovered and the olefins concentrated and separated by distillation or other techiques well understood in the art.

The major objective of the present work is to determine the effects of catalyst particle size on catalyst activity, coke production and hydrocarbon selectivity. The following examples will serve to illustrate the process of the invention without limiting the same.

EXAMPLES

An isothermal fixed-bed reactor system was utilized to obtain the experimental data. The unit consisted of two ¼" interior diameter stainless steel U-tube reactors connected in series. The first reactor, containing gamma-alumina, served as a methanol dehydration unit producing an equilibrium mixture of methanol, water and dimethyl ether. The second reactor, containing HZSM-5C catalyst, partially converted this equilibrium mixture to hydrocarbons. Each reactor was immersed in a separate fluidized sand bath. The reactor temperature was monitored at both the inlet and outlet of the catalyst bed, as well as at three external positions along the axis of the reactor.

The zeolite catalyst was prepared in a conventional manner. The catalyst contained 65 wt. % of HZSM-5C zeolite based material found in an aluminum matrix. All catalysts were presteamed for 5 hours at 1000° F.

The following experimental parameters were maintained throughout each run:

| | |
|---|---|
| Feed = | 50/50 water/MeOH |
| Temperature = | 600° F. |
| Pressure = | 25 psig |
| Conversion = | 50% ($CH_2$ oxygenates) |

A constant conversion level was maintained by adjusting WHSV with time to compensate for catalyst deactivation.

In order to determine the effect of catalyst particle size on catalyst activity and hydrocarbon selectivity, a series of runs were performed under essentially identical reaction conditions, utilizing catalysts with various effective particle sizes. Feed composition, reaction temperature, and reaction pressure were fixed at the same values for each run. Conversion, based on $CH_2$ oxygenates, was maintained at a constant value by decreasing WHSV, with respect to time on stream, to compensate for catalyst deactivation. The experimental procedure provided a uniform spatial environment with respect to concentration of reactants, intermediates and products during any particular run. Each experiment was terminated after the catalyst had converted approximately the same amount of reactants. By employing these experimental procedures, accurate catalyst comparisons were attainable.

Four different sizes of catalyst were examined. Both ⅛" and 1/16" cylindrical extrudates, sized to ⅛" nominal length, were used. A portion of the ⅛" diameter material was "halved" by cleaving the presized extrudate along its axis. Part of the 1/16" diameter material was "crushed" and screened to 18–28 mesh (0.0390–0.0234" diameter) particles. Table 1 lists pertinent particle size information for the four catalysts examined.

TABLE 1

| | | Catalyst Dimensions | |
|---|---|---|---|
| Example | Catalyst Description | Equivalent[a] Diameter (in.) | Volume/Surface Ratio (in.) |
| 1 | ⅛" dia. whole extrudate | 0.153 | 0.0208 |
| 2 | ⅛" dia. halved extrudate | 0.129 | 0.0146 |
| 3 | 1/16 " dia. whole extrudate | 0.0988 | 0.0125 |
| 4 | 18–28 mesh[b] | 0.0312 | 0.00520 |

[a]Equivalent particle diameter is the diameter of a shpere having the same external surface area as the particle in question.
[b]1/16"diameter material crushed and screened to 18–28 mesh (0.0390–0.0234" diameter) particles. Crushed particles are assumed to be spheres with a nominal diameter of 0.0312".

The effects of catalyst particle size on hydrocarbon product distribution are shown on Table 2 following. Table 2 illustrates that over the range of catalyst particle sizes examined, catalyst particle size does not affect any portion of the hydrocarbon product distribution at least at the 50% conversion level. For example, ethylene and propylene selectivities remained constant at about 26.2 and 22.8 hydrocarbon wt. %, respectively. Table 2 also illustrates that reactor pressure drop can be reduced while not adversely affecting hydrocarbon selectivity by employing ⅛" extrudates.

TABLE 2

| | Weight Percent of Total Hydrocarbon | | | |
|---|---|---|---|---|
| Example | 1 | 2 | 3 | 4 |
| Methane | 0.6 | 0.7 | 0.6 | 0.8 |
| Ethylene | 26.6 | 25.9 | 25.9 | 26.2 |
| Ethane | 0.1 | 0.1 | 0.1 | 0.1 |
| Propylene | 22.8 | 22.8 | 22.5 | 22.8 |
| Propane | 4.0 | 3.9 | 3.9 | 3.8 |
| Buteness | 8.7 | 8.7 | 7.9 | 8.4 |
| Isobutane | 4.0 | 4.3 | 3.9 | 4.2 |
| n-butane | 1.6 | 1.8 | 2.6 | 1.6 |
| Pentenes | 2.5 | 2.5 | 2.4 | 2.4 |
| $C_5$ P + N | 6.8 | 6.8 | 7.1 | 7.1 |
| $C_6$ P + N | 4.7 | 4.7 | 5.1 | 4.6 |
| $C_6$ O | 0.7 | 0.8 | 0.6 | 0.9 |
| $C_7$ P + N | 3.0 | 3.2 | 3.2 | 3.1 |
| $C_8$ P + O + N | 1.8 | 1.8 | 2.1 | 1.7 |
| $C_7$ O | 0.9 | 0.6 | 0.7 | 0.8 |
| $C_8$ P ;30 O + N | 1.8 | 1.8 | 2.1 | 1.7 |
| $C_9$ P + O + N | 1.0 | 1.1 | 1.3 | 1.1 |
| $C_{10}$ P + O + N | 1.0 | 0.9 | 1.1 | 0.7 |
| $C_{11}$ P + O + N | 0.0 | 0.0 | 0.0 | 0.0 |
| Benzene | 0.1 | 0.1 | 0.1 | 0.1 |
| Toluene | 0.4 | 0.4 | 0.5 | 0.4 |
| $C_8$ Aro | 3.2 | 3.3 | 3.5 | 3.0 |
| $C_9$ Aro | 1.8 | 1.9 | 2.1 | 1.8 |
| $C_{10}$ Aro (-durene) | 1.0 | 0.5 | 0.5 | 0.4 |
| Durene | 1.0 | 1.5 | 1.8 | 1.6 |
| $C_5^+$ Unknowns | 1.7 | 1.7 | 0.4 | 2.4 |
| $C_4^-$ (total) | 68.3 | 68.0 | 67.4 | 68.0 |
| $C_5^+$ (total) | 31.7 | 32.0 | 32.6 | 32.0 |

The effect of catalyst particle size on catalyst activity at 50% conversion is illustrated on Table 3 following.

TABLE 3

| | Catalyst Parameters at 50% Conversion | |
|---|---|---|
| Example | $WHSV_o$ (g $CH_2$/g Cat-hr) | $k_{SFO}$ ($hr^{-1}$) |
| 1 | 1.14 | 0.790 |
| 2 | 0.635 | 0.440 |
| 3 | 0.588 | 0.408 |
| 4 | 0.554 | 0.384 |

The $WHSV_o$ corresponds to the initial (t=0) WHSV required to yield 50% conversion. This extrapolation, which corresponds to initial catalyst activity, provides a common basis for catalyst comparison. The $k_{SFO}$ represents the pseudo-first-order rate constant calculated for the catalyst. In other words, the catalyst activity (effectiveness factor) is found to increase with particle size, in contrast to the expected catalyst size effect for pseudo-first-order reactions, with no intraparticle temperature gradients (lower effectiveness factor). In fact, a twofold increase in activity exists, at the 50% integral conversion level, between the crushed and ⅛" particle extremes examined in the present invention.

The spent catalyst carbon in coke results at approximately 50% overall conversion is summarized on Table 4.

TABLE 4

| | Carbon in Coke on the Catalyst Conversion Reactor Profiles and Yields | | | | | |
|---|---|---|---|---|---|---|
| Example | MeOH Converted (g) Mass Catalyst (g) | Average $CH_2$ Conversion (%) | C in Coke (wt %)[a] Inlet | Middle | Outlet | Coke Yield (wt %)[b] |
| 1 | 147 | 51.2 | 1.66 | 2.36 | 3.00 | 0.0159 |
| 2 | 157 | 51.8 | 0.58 | 2.34 | 3.95 | 0.0146 |
| 3 | 118 | 59.0 | 0.72 | 2.48 | 3.78 | 0.0197 |
| 4 | 150 | 54.7 | 0.50 | 2.12 | 4.50 | 0.0158 |

[a] C in Coke = (wt C/wt catalyst) × 100
[b] Coke Yield = (wt C/wt MeOH converted) × 100

Each spent catalyst exhibits a typical ascending coke profile along the axis of the conversion reactor associated with the MTC partial conversion mode of operation. In contrast to the MTG band-wise aging phenomenon, MTC aging is more uniform throughout the bed. The ascending coke profile suggests that certain conversion products, presumably the olefinic intermediates whose concentrations increase along the reactor, are coke precursors. As illustrated in the second column of Table 4, with the possible exception of Example 3, each catalyst accomplished approximately the same amount of conversion work; therefore, coke profiles and coke yields may be directly compared. The steepness of these profiles is inversely related to catalyst activity, i.e., the least active catalysts have the steepest profiles. The three smallest catalysts examined, Examples 2-4, exhibit essentially the same coke profiles. However, Example 1, i.e., the larger particle size catalyst, is not as steep as those of the smaller counterparts. Additionally, coke production is enhanced toward the front of the reactor beds containing the more active, large particle size catalyst. A study of the column entitled "Coke Yield" shows that although the spatial distribution of coke is related to catalyst activity and therefore particle size, the overall coke production in the reactor bed is essentially independent of these factors if the same amount of conversion work has been performed. Increased particle size does not seem to alter normal catalyst coke deactivation.

Without wishing to be limited to any particular theory, it is conceivable that the unexpected success of the present invention may be due to the interparticle transport effects coupled with an autocatalytic rate mechanism, which may explain the existing relationship between catalyst activity and particle size. The reactor temperature effects and non-isothermality cannot account for the observed activity increase. For pseudo-first-order reaction kinetics at 600° F. (315° C.), a 23° F. (13° C.) increase in reaction temperature is required to double MTC reaction rate for an MTC activation energy of 38 kcal/gmole oxygenate. A temperature rise of this magnitude has not previously been observed when experiments were performed with larger particles. Additionally, better heat transfer coefficients for the ⅛" catalyst would be expected because of the effect of increased space velocity, which may be offset to some degree by poor packing of the ⅛" catalyst particles in a ¼" tubular reactor. A preliminary autocatalytic kinetic model for the MTC process has the following form:

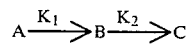

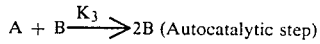

A + B $\xrightarrow{K_3}$ 2B (Autocatalytic step)

A—$CH_2$ in oxgenates
B—light olefins ($C_2$=, $C_3$= and $C_4$= lumped together)
C—other olefins and hydrocarbons
Using the above reaction scheme and the following diffusion theory, the behavior of a single catalyst particle can be simulated.

$$\nabla^2 \underline{D}C = \underline{K}C$$

$$D_A \frac{d^2 C_A}{dZ^2} = K_1 C_A + K_3 C_A C_B = (r_A)$$

$$D_B \frac{d^2 C_B}{dZ^2} = K_2 C_B - K_1 C_A - K_3 C_A C_B$$

$$D_C \frac{d^2 C_C}{dZ^2} = -K_2 C_B$$

where
Z = particle dimension;
$D_A$, $D_B$, $D_C$ = diffusion coefficients of A, B and C respectively;
At Z=0, $$\frac{dC_A}{dZ} = \frac{dC_B}{dZ} = \frac{dC_C}{dZ} = 0;$$

and
At Z=L, $C_A = C_{Ao}$; $C_B = C_{Bo}$; $C_C = C_{Co}$
The observed activity of a catalyst particle is given by an effectiveness factor, which is defined below:

Effectiveness Factor =

$$\frac{\text{Integral rate of methanol conversion inside a particle}}{\text{Rate of reaction in absence of intraparticle diffusion}}$$

A mathematical formula was devloped to estimate the effectiveness factor of a single particle. Using this model, the behavior of a single particle at various locations in the reactor for different particle sizes was simulated in a computer simulator study. The results from the computer simulation study are presented in the FIGURE. The ordinate is effectiveness factor and the abscissa is particle size. X corresponds to the location of the catalyst particle in the reactor. The integral conversions of the feedstock in the simulated reactor is 50% at the exit. Additionally, 1/16", ⅛" and ¼" extrudate particle sizes are marked on FIG. 1.

The dotted line in FIG. 1 corresponds to the integral average effectiveness factor for the reactor, based on calculations at five locations in the reactor (X=0, 0.25, 0.5, 0.75, 1, where 0 is the beginning of the reactor and 1 is the end). This corresponds to the observed increase in activity at 50% conversion. From the simulation study, at ⅛" particle is about 3 times more active than a 1/16" particle at 50% integral conversion level. The results are in qualitative agreement with the experimental observations recorded above.

Several conclusions can be drawn as a result of the information derived from FIG. 1: (1) particle size has pronounced effect on effectiveness factor at the front of a reactor where autocatalysis dominates (X=0); (2) the effectiveness factor increases with increasing particle size up to ¼" size for particles at the front of a reactor; and (3) the effectiveness factor decreases with increase in particle size for particles toward the exit of a reactor where autocatalysis is not present. Thus, it is apparent that a partial conversion, e.g., 50% conversion, ¼" extrudates are most effective for methanol conversion. Thus, under identical conditions, larger particles would allow higher space velocity operation, reducing the catalyst amount and cost per unit methanol converted. Therefore, the use of larger particles, i.e., greater than the standard 1/16" extrudate, shows beneficial results in the MTC fixed bed reactor. The concepts presented herein are applicable to both tubular heat-exchanger or multi-stage adiabatic reactors. It can be shown that the desired average particle size of the reactors described herein is dependent upon the desired conversion level of the feed. A further improvement brought out by the FIGURE may be to include particles of progressively decreasing sizes within a reactor. For example, in a single stage reactor, it may be advantageous to have larger particles at the entry point of the reactor catalyst bed followed by catalyst particles of decreasing sizes. In a multi-stage reactor, the first stage may have larger particle sizes, i.e., ¼", with the second and successive stages having corresponding decreasing particle size, i.e., ⅛", 1/16", etc.

The interaction of intraparticle diffusion and autocatalysis to obtain higher activity in larger particles can be applied to any process exhibiting autocatalysis. The MTC process in a fixed-bed reactor system would apply here. The use of larger particles allows for the operation of the process at lower operating pressures, thus maximizing light olefin yields and reducing the cost of catalyst per unit methanol conversion. Therefore, under identical conditions, larger particles would allow higher velocity operation, reducing the catalyst amount and cost per unit methanol converted. The use of larger particles, greater than 1/16", is recommended in the MTC fixed bed reactors. These concepts are applicable to both tubular heat-exchanger or multi-stage adiabatic reactors.

In addition to the activity benefits of larger particles, one would also expect improvement in reactor stability due to lower pressures in the reactor and in situ light olefin cofeeding due to the presence of light olefins inside the catalyst.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. In a process for converting a feed comprising at least one lower aliphatic alcohol having from 1 to 3 carbon atoms and/or corresponding ethers of such alcohols, alone or in admixture with water, to hydrocarbon products comprising olefins, said process comprising contacting said feed in a reaction zone with a crystalline silicate zeolite catalyst, withdrawing from said reaction zone an effluent comprising light olefins, and separating said light olefins from said effluent, the improvement comprising controlling the activity of the catalyst by selecting the particle size of said crystalline silicate zeolite catalyst wherein the activity of said catalyst in said process increases with increasing catalyst particle size.

2. The process of claim 1, wherein said aliphatic alcohol having from 1 to 3 carbon atoms is methanol and said ether is said dimethyl ether.

3. The process according to claim 1, wherein said aliphatic alcohol having from 1 to 3 carbon atoms is ethanol.

4. The process according to claim 1, wherein said crystalline silicate zeolite is selected from the group consisting of HZSM-5, HZSM-11, HZSM-12, HZSM-21, HZSM-35, HZSM-38, and HZSM-48.

5. The process according to claim 1, wherein said crystalline silicate zeolite is HZSM-5.

6. The process according to claim 1, wherein said feed is first contacted with a dehydration catalyst at elevated temperatures to obtain a product comprising a mixture of water and at least one ether.

7. The process of claim 6, wherein said dehydration catalyst is gamma-alumina.

8. The process according to claim 1, wherein the average particle size of said zeolite catalyst is at least ⅛" at a 50% conversion level of said feed.

9. In a process for converting a feed comprising at least one lower aliphatic alcohol having from 1 to 3 carbon atoms and/or corresponding eithers of such alcohols, wherein said feed is first contacted with a dehydration catalyst at elevated temperatures in a first reaction zone to obtain a product comprising a mixture of water and at least one ether, and said product of said first reaction zone is thereafter contacted with a crystalline silicate zeolite catalyst in a second reaction zone, said zeolite having a silica-to-alumina ratio of at least about 12, and a Constraint Index of about 1 to 12, withdrawing from said second reaction zone an effluent comprising a mixture of light olefins, paraffin, hydrocarbons and aromatic hydrocarbons, and segregating said light olefins from said effluent, the improvement comprising controlling the activity of the catalyst by selecting the particle size of said crystalline silicate zeolite catalyst wherein the activity of said catalyst increases with increasing catalyst particle size.

10. The process according to claim 9, wherein said feed comprises methanol and said ether comprises dimethyl ether.

11. The process according to claim 9, wherein said dehydration catalyst is gamma-alumina and said crystalline silicate zeolite in said second reaction zone is ZSM-5 zeolite.

12. The process according to claim 9, wherein the average particle size of said zeolite catalyst is at least ⅛" at a 50% conversion level of said feed.

* * * * *